(12) United States Patent
Venturini et al.

(10) Patent No.: US 7,226,449 B2
(45) Date of Patent: Jun. 5, 2007

(54) RING FIXATOR

(75) Inventors: Daniele Venturini, Povegliano Veronese (IT); Michele Coati, San Pietro In Cariano (IT); Graziano Rossi, Verona (IT)

(73) Assignee: Orthofix S.r.l. (IT)

( * ) Notice: Subject to any disclaimer, the term of this patent is extended or adjusted under 35 U.S.C. 154(b) by 525 days.

(21) Appl. No.: 10/275,774

(22) PCT Filed: May 8, 2001

(86) PCT No.: PCT/EP01/05213

§ 371 (c)(1),
(2), (4) Date: Jun. 27, 2003

(87) PCT Pub. No.: WO01/85041

PCT Pub. Date: Nov. 15, 2001

(65) Prior Publication Data

US 2004/0116926 A1    Jun. 17, 2004

(30) Foreign Application Priority Data

May 9, 2000    (EP)    .................................... 00830339

(51) Int. Cl.
A61B 17/00    (2006.01)
A61F 4/00    (2006.01)
A61F 5/04    (2006.01)

(52) U.S. Cl. ...................................................... 606/56
(58) Field of Classification Search ................... 606/56, 606/54, 55, 57–59
See application file for complete search history.

(56) References Cited

U.S. PATENT DOCUMENTS 5,074,866 A * 12/1991 Sherman et al. .............. 606/56
5,405,347 A *  4/1995 Lee et al. ...................... 606/54
5,429,637 A *  7/1995 Hardy .......................... 606/54

FOREIGN PATENT DOCUMENTS

EP    0481697 A1    4/1992
WO    WO-97/30650 A1    8/1997

OTHER PUBLICATIONS

Schwartsmann,V. et al., Techniques of Fracture Reduction: The Ilizarov Method, Techniques Orthop., vol. 5, No. 4, Dec. 1990, pp. 53-59, Gaithersburg, MD, US.
Green, S., Components of the Ilizarov System, Techniques Orthop., vol. 5, No. 4, Dec. 1990, pp. 1-11, Gaithersburg, MD, US.

* cited by examiner

Primary Examiner—William H Matthews
(74) Attorney, Agent, or Firm—Akerman Senterfitt

(57) ABSTRACT

An external fixator apparatus (1) of the ring type for stabilizing bone fractures, including at least one pair of rings (6, 7), of which one (6) is proximal and the other (7) is distal, and at least one tie rod (8, 9, 10) interconnecting the rings (6, 7) to each other. The rod (8, 9, 10) is split into two rod sections (11, 12) connected together by a joint (21) and the joint (21) includes a pivot mount (22) having a predetermined axis (x—x) for the angular displacement of the rod sections (11, 12), and a sliding mount (23) according to a pre-determined sliding direction (y—y) for offsetting the rod sections (11, 12).

7 Claims, 4 Drawing Sheets

RING FIXATOR

FIELD OF THE INVENTION

This invention broadly relates to an external fixator apparatus of the ring type for stabilizing bone fractures.

In a particular embodiment, the invention provides a ring fixator apparatus of the type specified in the preamble of the main claim.

As it is known, there is the necessity to set the mutual position of the rings, depending on the type of treatment to apply or on a particular fracture to stabilize.

PRIOR ART

A prior type of known ring fixator apparatuses currently in use comprises rings which are connected with each other by telescoping tie rods adapted to be extended as required. Such fixator apparatuses are of simple construction and are suitable for ready adjustment of the ring spacing, but are useless when the rings need to be mutually set for a greater manoeuvring freedom, e.g. when the inclination of the rings to each other needs to be changed.

Also available are splint apparatuses wherein the rings are connected by the so-called tie plates, in the form of perforated metal strips. The tie plates afford a wider adjustment of the mutual position of the rings, but are bulky and awkward to manipulate. Fixator apparatuses have been proposed wherein the tie rods have their opposite ends connected to the rings through respective hinges, so that a desired mutual positional setting of the rings can be obtained. However, this arrangement results in the construction of a heavy and expensive fixator apparatus.

PCT application No. WO 97/30650 discloses an external fixator whose two rings are linked to one another by means of triplets of rod sections, wherein the rod sections of each triplet are connected together by two locking joints, which allow to modify the inclination of the rings to one another but does not enable to rotate the rings with respect to one another. Moreover, the handling of such an apparatus is quite complicate due to the high number of joints to be locked.

European application No. EP 0 481 697 discloses an external fixator whose two rings are linked to one another by means of pairs of tie rod sections, wherein the rod sections of each pair are connected together by an adjustment device. The latter allows to translate or rotate the rings with respect to one another but does not permit to modify the inclination of the rings to one another.

Another known apparatus, which only allows to translate or rotate the rings but not to modify their inclination with respect to one another, is disclosed in Schwartsman V. et al. "Techniques of fracture reduction: the Ilizarov method", Techniques in Orthopaedics, US, Gaithersburg, Md., vol. 5, no. 4, pages 53–59. This apparatus is quite complicate to manipulate due to the absence of any sliding joints.

The underlying technical problem of this invention is to contrive a ring fixator apparatus as indicated with such structural and functional features as to fill the demand, at the same time overcoming the shortcomings mentioned hereinabove with reference to the prior art.

SUMMARY OF THE INVENTION

Such a problem has been solved by the provision of a fixator apparatus comprising at least one pair of rings, of which one is proximal and an other is distal, and at least one tie rod interconnecting the rings to each other, wherein said at least one rod is split into two rod sections connected together by a joint and said joint comprises a pivot mount having a predetermined axis for the angular displacement of the rod sections and comprises a slide mount according to a predetermined sliding direction for offsetting the rod sections.

Further features and advantages of a fixator apparatus according to this invention will be apparent in the following description of a preferred embodiment thereof, given by way of non-limitative example with reference to the accompanying drawing figures.

DETAILED DESCRIPTION

Figure 1:
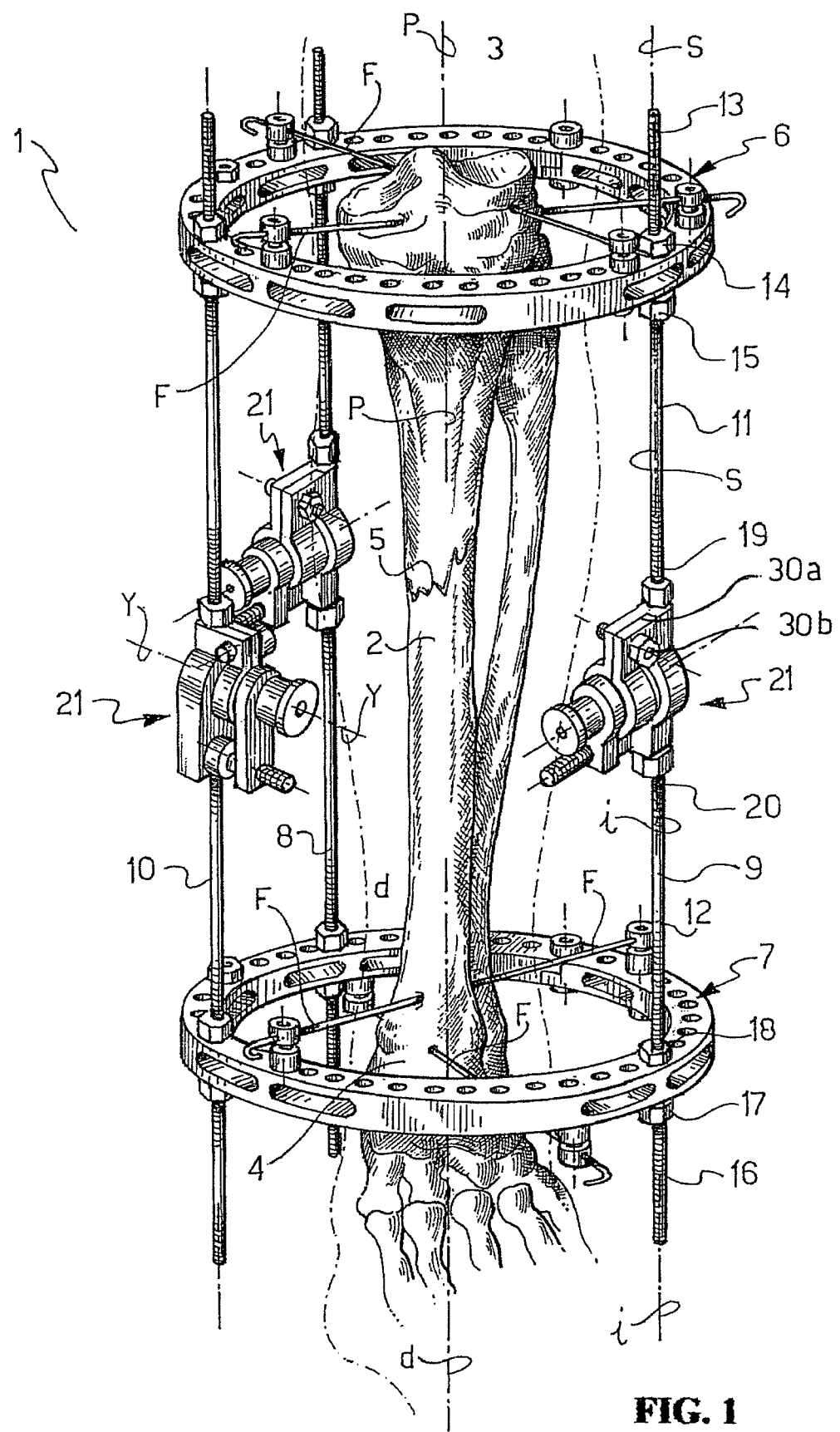
FIG. 1 shows a perspective view of a ring fixator apparatus according to the invention.
Figure 2:
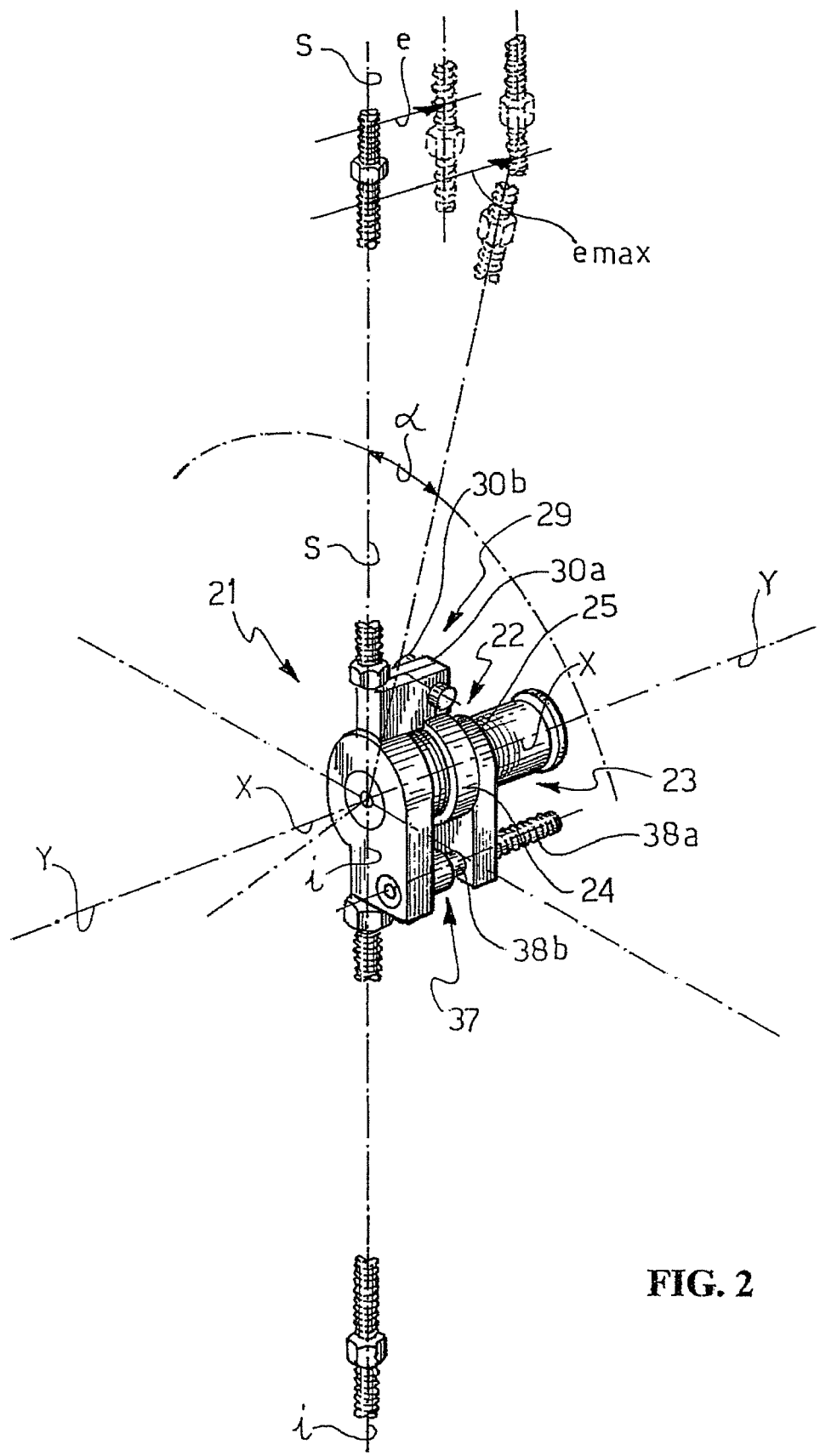
FIG. 2 shows a perspective view, drawn to an enlarged scale, of a particular of the fixator device shown in FIG. 1.
Figure 3:
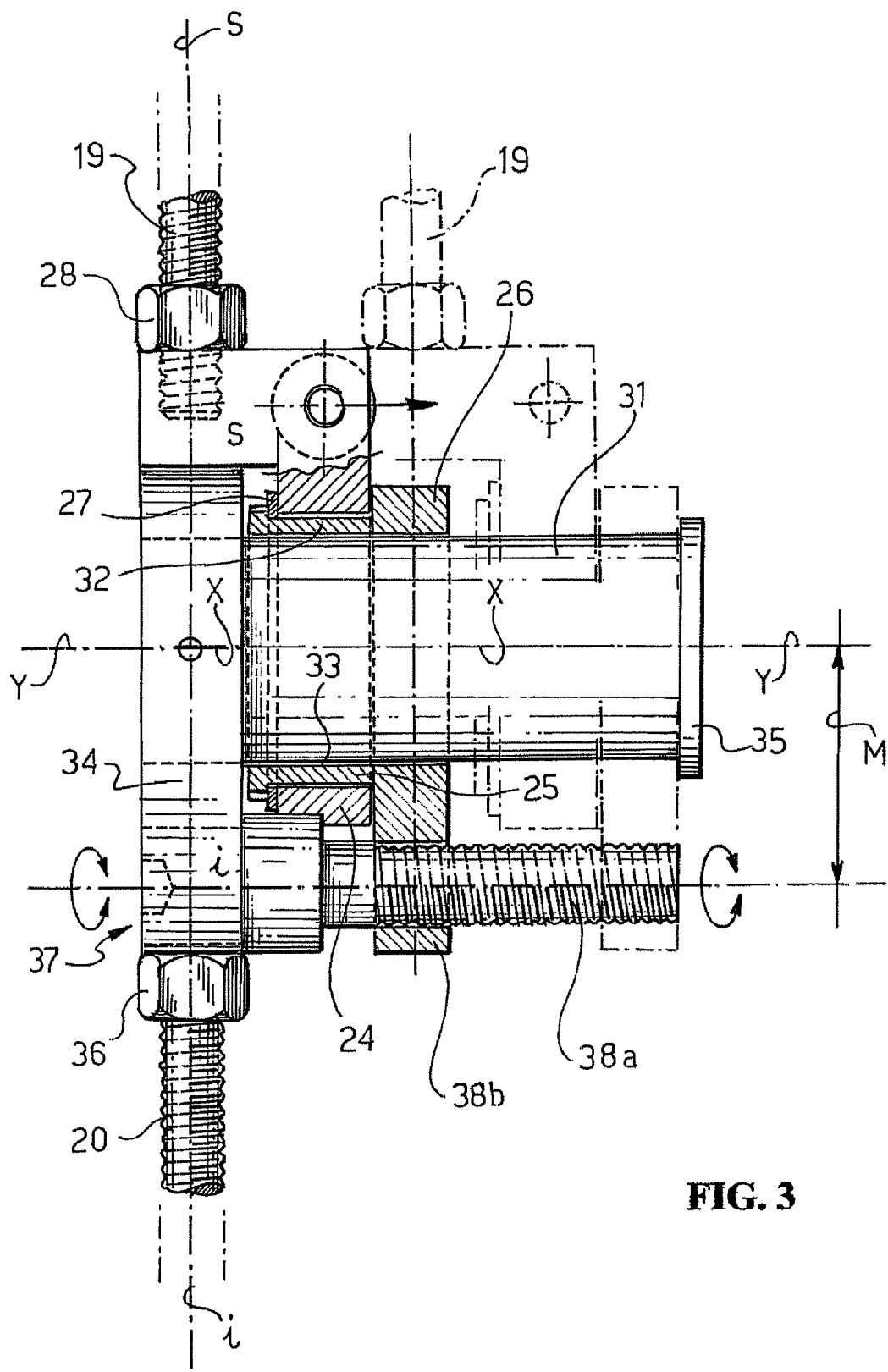
FIG. 3 shows a sectional view of the particular of FIG. 2 taken along line III—III.

In the drawing views, a fixator device according to the invention is shown overall at 1, and is of the external ring type intended for stabilizing bone fractures.

In the example, the fixator apparatus 1 is applied to a tibia 2 having a proximal end 3, a distal end 4, and a middle portion including a brake 5.

The fixator 1 comprises a pair of rings, namely a proximal ring 6 and a distal ring 7, and comprises three tie rods 8, 9 and 10 connecting the rings 6 and 7 together.

The rings 6 and 7 are identical and circular in the example, and have a predetermined diameter. Their axes p—p and d—d, respectively, are coincident in a first condition of operation of the fixator apparatus, that is with the rings 6 and 7 exactly superposed on each other.

One end 3, 4 of the tibia 2 is secured to each ring 6, 7, respectively, by means of appropriate linking elements, in the form of wires F in the example.

The tie rods 8, 9 and 10 are identical and essentially extend along parallel directions to the axes p—p and d—d.

In general, two of the rods 8, 9 and 10, precisely the rods 8 and 9, occupy diametrically opposed positions, while the third rod 10 is positioned at 90°.

Each of the tie rods 8, 9 and 10 of the fixator apparatus 1 according to the invention is split in two rod sections. In other words, it is split into two rod sections and comprises an upper rod section 11 and a lower rod section 12 extending along respective axes s—s and i—i. Both rod sections 11 and 12 have the same length and are in the form of a threaded stock.

The upper rod section 11 has a top end 13 fastened to the upper ring 6 by means of a nut 14 and a locknut 15.

The lower rod section 12 has a bottom end 16 which is likewise fastened to the lower ring 7 by means of a nut 17 and a locknut 18.

In each of the rods 8, 9 and 10, the upper section 11 has a bottom end 19, and the lower section 16 has a top end 20. Said ends 19 and 20 are connected to each other by a joint, overall designated at 21, to be described. In FIG. 1, the joint of the rod 10 is shown according to a 90° rotation as to the joints of the rods 8 and 9 in order to make visible its other side more conveniently.

The joint 21 approximately locates at a mid-length of each rod. In particular, the joint 21, which connects the rod section 11 to the rod section 12, overall comprises a pivot mount 22 and a slide mount 23.

The pivot mount 22 has an axis x—x perpendicular to the axes s—s and i—i of the rod sections 11 and 12, and comprises a sleeve member 24 which is mounted for free rotation about a bush 25 and held snugly in the axial direction between a collar 26 formed integrally with the bush 25 and a snap ring 27 mounted on the bush.

The rod section 11 has its bottom end 19 engaged threadably in the sleeve member 24 and retained therein by a locknut 28.

The top end 20 of the lower rod section 12 is engaged in the bush 25 in a manner to be described.

It should be noted that the pivot mount 22 comprises a locking arrangement 29 for its locking in a predetermined angular position, so that a set angle α is firmly formed between the axes s—s and i—i of the rod sections. In particular, the locking arrangement 29 comprises a slit 30a in the sleeve 24 and a hand-operated clamp screw 30b extended across the slit 30a.

The slide mount 23 comprises a straight slide way 31 defining a slide axis y—y which is coincident with the pivot axis x—x, and a slider 32 arranged to axially slide along the slide way 31. The slider 32 is realized in the bush 25 which is bored at 33 to fit snugly onto the slideway 31.

In the example, the bore 33 and the slide way 31 have circular cross-sectional shapes.

The stroke length of the slider 32 along the slide way 31 is limited by first 34 and second 35 end collars, which are integral with the slide way 31 at the extremities thereof, and forming travel limiters for the slider.

The lower rod section 12 is fixed to the end collar 34, with its top end 20 engaged threadably in the collar and retained by a locknut 36.

Adjustment means 37 is provided for shifting the slider 32 along the slideway 31 and for holding it firmly in a desired predetermined attained position thereon. In particular, the adjustment means 37 comprises an actuating screw 38a which has an axis v—v lying parallel to the axis y—y at a distance "M" away therefrom, can be manually operated, and is rotatably retained by the collar 34. It further comprises a thread way 38b formed in the collar 26 and engaged in the spin by the actuating screw 38a.

Thus, an offset "e" can be established between the rods within a predetermined range. In particular, the offset is zero, that is the rod axes s—s and i—i are aligned, when the slider 32 is abutting against the collar 34, while it has the maximum offset "emax" (in the example 10 mm) when the slider 32 is abutting against the collar 35.

The actuating screw 38a, being offset by the distance "M" from the axis y—y of the slideway 31, provides a stop against the rotation of the slider 32 around the axis of the slideway 31, and biases the sliding mount 23 of the prismatic type.

It should be noted that, according to another aspect of the invention, the sleeve 24 and the bush 25 are made of a material selected among materials transparent to X-radiation, i.e. transparent to X-rays, such as a thermoplastic polietherterketone resin, known as Peek, with a 30-percent fill of carbon fibers; thus, the whole pivot mount 22 is overall transparent to X-radiation. Similarly the slideway 31 and the slider 32 are made of a transparent material to X-radiation so that, as a result, also the sliding mount 23 is altogether made transparent to X-radiation. Ultimately, the whole joint 21 will therefore be transparent to X-radiation.

It will be appreciated how, thanks to the above-described structure of the ring fixator apparatus according to the invention, to the proximal ring can be given any desired setting as regards to the distal ring, in base of the type of treatment to be apply or of the specific bone fracture to stabilize, both as regards their spacing and their mutual inclination, or twist, or offset.

The ring spacing can be readily adjusted by acting on the tie rods themselves, that is on the rod sections 11, 12 formed by threaded stocks, through the nuts and the locknuts 14, 15 and 17, 18 used for fastening them to the rings.

Figure 4:
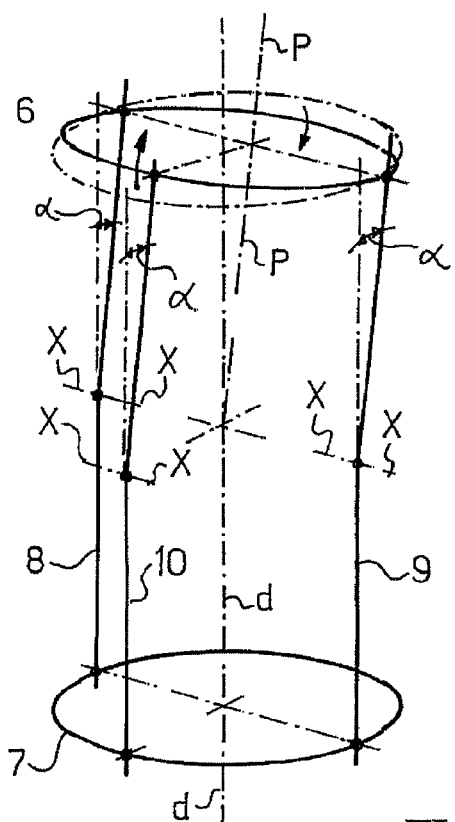
FIGS. 4, 5 and 6 schematically show perspective views illustrating different settings of the fixator device of FIG. 1 in operation.

The mutual ring inclination can be adjusted by acting on the rod 10, specifically on the nuts and locknuts used for fastening a rod section to the ring,while the pivot mounts of the diametrically opposite rods 8 and 9 are easily locked at a corresponding angle α (see FIG. 4).

Figure 5:
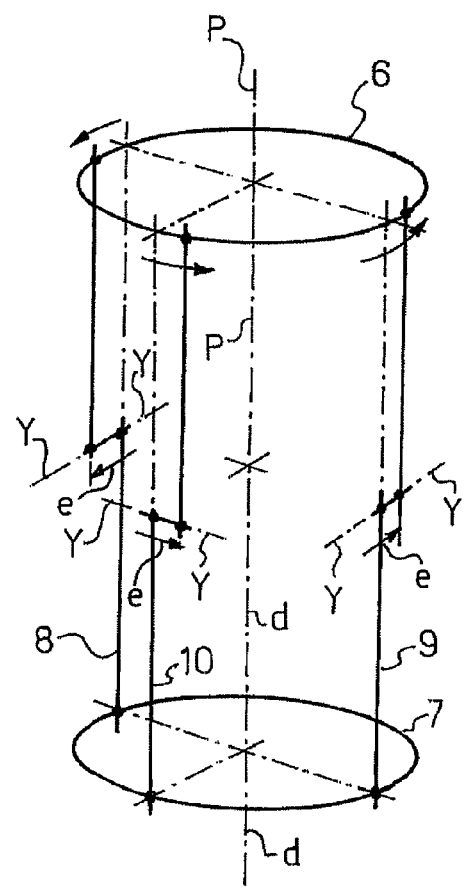

The twist can be adjusted by acting on the slide mounts 23 of the joints 21 of the three rods 8, 9 and 10 (see FIG. 5), which are pre-set to have their sliding directions y—y substantially tangent with the rings.

Figure 6:
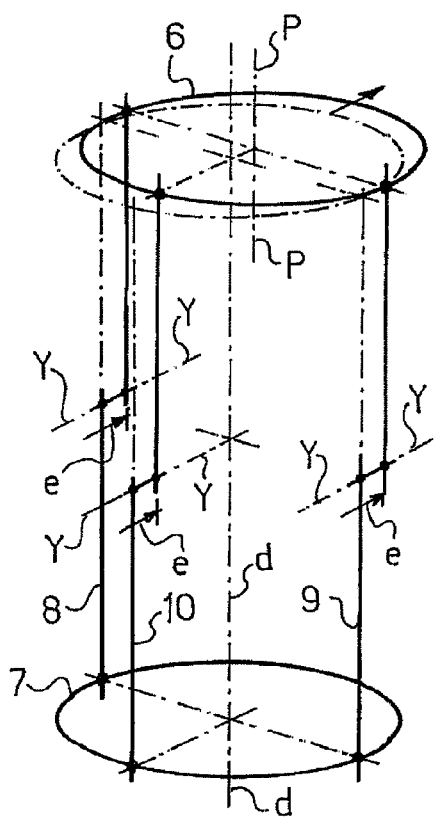

Lastly, the offset can be adjusted by acting on the slide mounts 23 of the joints 21 of the three rods 8, 9 and 10 (see FIG. 6), which are pre-set with their axes y—y lying all parallel.

The main advantage of the ring type fixator apparatus according to the invention lies, therefore, in the extremely wide adjustment capacity of manual settings provided for the rings.

Another advantage is its uniquely simple structure and its lightweight.

The adjustments can be easily made without interfering with the operation of X-ray apparatus, on account of the joint being transparent to X-radiation.

A further advantage is its compact design, i.e. its particularly small overall dimensions, a non-negligible advantage for an external type of fixator device.

It should be further noted that the invention can be retro-fitted to fixator apparatuses using most of their existing parts, such as the rings, by merely replacing their tie rods.

In order to fulfil contingent and specific requirements, a skilled person of the field can obviously make many changes and modifications to the above-described fixator apparatus. Such changes and modifications are covered by the protection scope of the invention as defined in the following claims.

The invention claimed is:

1. An external ring fixator apparatus for stabilizing bone fractures, comprising:
   at least one pair of rings, of which one is proximal and another is distal; and
   at least one tie rod interconnecting the rings to each other, wherein said at least one rod is split into two rod sections connected together by a joint,
   wherein said joint comprises a pivot mount having a predetermined axis for the angular displacement of the rod sections and comprises a sleeve,
   wherein the axis of the pivot mount lies perpendicularly to said rod sections,
   wherein an offset between the rod sections is obtained by means of a slide mount having a predetermined sliding direction for offsetting the rod sections, and comprising a slider slidably mounted on a slide way extending along the pivot mount axis, the sliding direction of the slide mount being coincident with the pivot mount axis, and wherein one end of one rod section is fixed to the slide way, and one end of the other rod section is fixed to the sleeve that is rotatably mounted on the slide way.

2. An external ring fixator according to claim 1, wherein the sleeve is rotatably mounted on a bush, itself slidably mounted on said slide way.

3. An external ring fixator apparatus for stabilizing bone fractures, comprising:

at least one pair of rings, of which one is proximal and an other is distal; and at least one tie rod interconnecting the rings to each other, wherein said at least one rod is split into two rod sections connected together by a joint, wherein said joint comprises a pivot mount having a predetermined axis for the angular displacement of the rod sections and comprises a slide mount according to a predetermined sliding direction for offsetting the rod sections, wherein said pivot mount comprises locking means for locking the rod sections in a predetermined angular position, and wherein the locking means of the pivot mount comprise a slit formed in the sleeve and a clamp screw extending across the slit.

4. An external ring fixator apparatus according to claim 1, wherein the slide mount includes an offset adjuster means.

5. An external ring fixator apparatus according to claim 4, wherein said adjuster means comprises an actuating screw and a threadway.

6. An external ring fixator apparatus according to claim 1, wherein the pivot mount is made of a material transparent to X-radiation.

7. An external ring fixator apparatus according to claim 1, wherein the slide mount is made of a material transparent to X-radiation.

* * * * *